United States Patent [19]

Hillman et al.

[11] Patent Number: 6,124,446
[45] Date of Patent: Sep. 26, 2000

[54] HUMAN VPS35/MEM3-RELATED PROTEIN

[75] Inventors: Jennifer L. Hillman; Neil C. Corley, both of Mountain View; Purvi Shah, Sunnyvale, all of Calif.

[73] Assignee: Incyte Pharmaceuticals, Inc., Palo Alto, Calif.

[21] Appl. No.: 09/005,180

[22] Filed: Jan. 8, 1998

[51] Int. Cl.$^7$ ............ C07H 21/02; C07H 21/04; G01N 33/53; C12N 15/09; C12N 1/20

[52] U.S. Cl. ............ 536/23.1; 536/23.2; 536/23.5; 536/23.4; 435/7.1; 435/69.2; 435/320.1; 435/325; 435/252.3; 435/252.33; 435/254.2; 435/419; 435/254.11

[58] Field of Search ............ 536/23.1, 23.2, 536/23.5, 23.4; 435/7.1, 69.2, 320.1, 325, 252.3, 252.33, 254.2, 419, 254.11

[56] References Cited

U.S. PATENT DOCUMENTS

| | | |
|---|---|---|
| 5,763,589 | 6/1998 | Hillman et al. . |
| 5,834,241 | 11/1998 | Hillman et al. . |
| 5,840,539 | 11/1998 | Hillman et al. . |
| 5,863,764 | 1/1999 | Hillman et al. . |
| 5,955,282 | 9/1999 | Hillman et al. . |
| 5,981,226 | 11/1999 | Hillman et al. . |
| 5,986,057 | 11/1999 | Hillman et al. . |
| 5,989,859 | 11/1999 | Bandman et al. . |

OTHER PUBLICATIONS

Pevsner et al Gene, 183: 7–14, 1996.
Jacobsen et al, JBC, 271/49: 31379–383, 1996.
Escola et al JBC, 273/32: 20121–20127, 1998.
Burd et al, Mol. & Cell. Biol. 16/5: 2369–377, 1996.
Paravicini et al, Biochemistry, 31: 7126–7133, 1992a.
Hwang et al., Mammalian Genome, Abstract only 7/8: 586–590, 1996.
Paravicini et al Mol. Briol. Cell. 3: 415–427MPSRCH→Accession#S5693 S56937, 1992.
Katsoulou et al Yeast 12: 787–797 MBSRCH Accession 190 571643, 1996.
Hudson MPSRCH Accession# G07015, 1995.
Wilson et al. Nature 368: 32–38 MPSRCH Accession # Q 21053, 1994.
Database EMBL, ID HSZZ12870, Accession No. AA307735, Apr. 18, 1997, SP002101816 (GI 1960063).
Database EMBL, ID HSAA97881, Accession No. AA191661, Jan. 21, 1997, XP002101817 (GI 1780332).
Database EMBL, ID HS1201462, Accession No. AA403194, May 1, 1997, XP002101818 (GI 2055710).

*Primary Examiner*—Nita Minnifield
*Attorney, Agent, or Firm*—Incyte Pharmaceuticals, Inc.

[57] ABSTRACT

The invention provides a human Vps35/Mem3-related protein (hvmrp) and polynucleotides which identify and encode hvmrp. The invention also provides expression vectors, host cells, antibodies, agonists, and antagonists. The invention also provides methods for treating or preventing disorders associated with expression of hvmrp.

2 Claims, 15 Drawing Sheets

```
5' A CTA GTT CTC TCT CTC TCT CCG CGG GAG GCT ACG CGC GGG GCG GGT GCT    54

GCT TGC AGG CTC TGG GGA GTC ATG CCT ACA ACA CAG TCC CCT CAG           108
                              M   P   T   T   Q   S   P   Q

GAT GAG CAG GAA AAG CTC TTG GAT GCC GAA GCC ATA CAG GCT GTG CAG TCA   162
 D   E   Q   E   K   L   L   D   A   E   A   I   Q   A   V   Q   S

TTC CAA ATG AAG AGA TGC CTG GAC AAA AAC AAG CTT ATG GAT GCT CTA AAA CAT  216
 F   Q   M   K   R   C   L   D   K   N   K   L   M   D   A   L   K   H

GCT TCT AAT ATG CTT GGT GAA CTC CGG ACT TCT ATG TTA TCA CCA AAG AGT TAC  270
 A   S   N   M   L   G   E   L   R   T   S   M   L   S   P   K   S   Y

TAT GAA CTT TAT ATG GCC ATT TCT GAT GAA CTG CAC TAC TTG GAG GTC TAC CTG  324
 Y   E   L   Y   M   A   I   S   D   E   L   H   Y   L   E   V   Y   L

ACA GAT GAG TTT GCT AAA GGA AGG AAA GTG GCA GAT CTC TAC GAA CTT GTA CAG  378
 T   D   E   F   A   K   G   R   K   V   A   D   L   Y   E   L   V   Q
```

FIGURE 1A

```
      387             396             405             414             423             432
TAT GCT GGA AAC ATT ATC CCA AGG CTT TAC CTT TTG ATC ACA GTT GGA GTT GTA
 Y   A   G   N   I   I   P   R   L   Y   L   L   I   T   V   G   V   V 441             450             459             468             477             486
TAT GTC AAG TCA TTT CCT CAG TCC AGG AAG GAT ATT TTG AAA GAT TTG GTA GAA
 Y   V   K   S   F   P   Q   S   R   K   D   I   L   K   D   L   V   E 495             504             513             522             531             540
ATG TGC CGT GGT GTG CAA CAT CCC TTG AGG GGT CTG TTT CTT CGA AAT TAC CTT
 M   C   R   G   V   Q   H   P   L   R   G   L   F   L   R   N   Y   L 549             558             567             576             585             594
CTT CAG TGT ACC AGA AAT ATC TTA CCT GAT GAA GGA GAG CCA ACA GAT GAA GAA
 L   Q   C   T   R   N   I   L   P   D   E   G   E   P   T   D   E   E 603             612             621             630             639             648
ACA ACT GGT GAC ATC AGT GAT TCC ATG GAT TTT GTA CTG CTC AAC TTT GCA GAA
 T   T   G   D   I   S   D   S   M   D   F   V   L   L   N   F   A   E 657             666             675             684             693             702
ATG AAC AAG CTC TGG GTG CGA ATG CAG CAT CAG GGA CAT AGC CGA GAT AGA GAA
 M   N   K   L   W   V   R   M   Q   H   Q   G   H   S   R   D   R   E 711             720             729             738             747             756
AAA AGA GAA CGA GAA AGA CAA GAA CTG AGA ATT TTA GTG GGA ACA AAT TTG GTG
 K   R   E   R   E   R   Q   E   L   R   I   L   V   G   T   N   L   V
```

FIGURE 1B

```
      765            774            783            792            801            810
CGC CTC AGT CAG TTG GAA GGT GTA AAT GTG GAA CGT TAC AAA CAG ATT GTT TTG
 R   L   S   Q   L   E   G   V   N   V   E   R   Y   K   Q   I   V   L 819            828            837            846            855            864
ACT GGC ATA TTG GAG CAA GTT GTA AAC TGT AGG GAT GCT TTG GCT CAA GAA TAT
 T   G   I   L   E   Q   V   V   N   C   R   D   A   L   A   Q   E   Y 873            882            891            900            909            918
CTC ATG GAG TGT ATT CAG ATT TTC CCT GAT GAA TTT CAC CTC CAG ACT TTG
 L   M   E   C   I   Q   I   F   P   D   E   F   H   L   Q   T   L 927            936            945            954            963            972
AAT CCT TTT CTT CGG GCC TGT GCT GAG TTA CAC CAG AAT GTA AAG AAC
 N   P   F   L   R   A   C   A   E   L   H   Q   N   V   K   N 981            990            999           1008           1017           1026
ATA ATT GCT TTA ATT GAT AGA TTA GCT TTA TTT GCT CAC CGT GAA GAT GGA
 I   I   A   L   I   D   R   L   A   L   F   A   H   R   E   D   G 1035           1044           1053           1062           1071           1080
CCT GGA ATC CCA GCG GAT ATT AAA CTT TTT GAT ATA TTT TCA CAG CAG GTG GCT
 P   G   I   P   A   D   I   K   L   F   D   I   F   S   Q   Q   V   A 1089           1098           1107           1116           1125           1134
ACA GTG ATA CAG TCT AGA CAA GAC ATG CCT TCA GAG GAT GTT GTA TCT TTA CAA
 T   V   I   Q   S   R   Q   D   M   P   S   E   D   V   V   S   L   Q
```

FIGURE 1C

```
      1143           1152           1161           1170           1179           1188
GTC TCT CTG ATT AAT CTT GCC ATG AAA TGT TAC CCT GAT CGT GTG GAC TAT GTT
 V   S   L   I   N   L   A   M   K   C   Y   P   D   R   V   D   Y   V
      1197           1206           1215           1224           1233           1242
GAT AAA GTT CTA GAA ACA ACA GTG GAG ATA TTC AAT AAG CTC AAC CTT GAA CAT
 D   K   V   L   E   T   T   V   E   I   F   N   K   L   N   L   E   H
      1251           1260           1269           1278           1287           1296
ATT GCT ACC AGT AGT GCA GTT TCA AAG GAA CTC ACC AGA CTT TTG AAA ATA CCA
 I   A   T   S   S   A   V   S   K   E   L   T   R   L   L   K   I   P
      1305           1314           1323           1332           1341           1350
GTT GAC ACT TAC AAC AAT ATT TTA ACA GTC TTG AAA TTA AAA CAT TTT CAC CCA
 V   D   T   Y   N   N   I   L   T   V   L   K   L   K   H   F   H   P
      1359           1368           1377           1386           1395           1404
CTC TTT GAG TAC TTT GAC TAC GAG TCC AGA AAG AGC ATG AGT TGT TAT GTG CTT
 L   F   E   Y   F   D   Y   E   S   R   K   S   M   S   C   Y   V   L
      1413           1422           1431           1440           1449           1458
AGT AAT GTT CTG GAT TAT AAC ACA GAA ATT GTC TCT CAA GAC CAG GTG GAT TCC
 S   N   V   L   D   Y   N   T   E   I   V   S   Q   D   Q   V   D   S
      1467           1476           1485           1494           1503           1512
ATA ATG AAT TTG GTA TCC ACG TTG ATT CAA GAT CAG CCA GAT CAA CCT GTA GAA
 I   M   N   L   V   S   T   L   I   Q   D   Q   P   D   Q   P   V   E
```

FIGURE 1D

```
     1521            1530            1539            1548            1557            1566
GAC CCT GAT CCA GAA GAT TTT GCT GAT GAG CAG AGC CTT GTG GGC CGC TTC ATT
 D   P   D   P   E   D   F   A   D   E   Q   S   L   V   G   R   F   I 1575            1584            1593            1602            1611            1620
CAT CTG CGC TCT GAG GAC CCT GAC CAG CAG TAC TTG ATT TTG AAC ACA GCA
 H   L   R   S   E   D   P   D   Q   Q   Y   L   I   L   N   T   A 1629            1638            1647            1656            1665            1674
CGA AAA CAT TTT GGA GCT GGT GGA AAT CAG CGG ATT CGC TTC ACA CTG CCA CCT
 R   K   H   F   G   A   G   G   N   Q   R   I   R   F   T   L   P   P 1683            1692            1701            1710            1719            1728
TTG GTA TTT GCA GCT TAC CAG CTG GCT TTT CGA TAT AAA GAG AAT TCT AAA GTG
 L   V   F   A   A   Y   Q   L   A   F   R   Y   K   E   N   S   K   V 1737            1746            1755            1764            1773            1782
GAT GAC AAA TGG GAA AAG AAA TGC CAG AAG ATT TTT TCA TTT GCC CAC CAG ACT
 D   D   K   W   E   K   K   C   Q   K   I   F   S   F   A   H   Q   T 1791            1800            1809            1818            1827            1836
ATC AGT GCT TTG ATC AAA GCA GAG CTG GCA GAA TTG CCC TTA AGA CTT TTT CTT
 I   S   A   L   I   K   A   E   L   A   E   L   P   L   R   L   F   L 1845            1854            1863            1872            1881            1890
CAA GGA GCA CTA GCT GGG GAA ATT GGT TTT GAA AAT CAT GAG ACA GTC GCA
 Q   G   A   L   A   G   E   I   G   F   E   N   H   E   T   V   A
```

FIGURE 1E

```
      1899        1908        1917        1926        1935        1944
TAT GAA TTC ATG TCC CAG GCA TTT TCT CTG TAT GAA GAT GAA ATC AGC GAT TCC
 Y   E   F   M   S   Q   A   F   S   L   Y   E   D   E   I   S   D   S 1953        1962        1971        1980        1989        1998
AAA GCA CAG CTA GCT GCC ATC ACC TTG ATT GGC ACT TTT GAA AGG ATG AAG
 K   A   Q   L   A   A   I   T   L   I   G   T   F   E   R   M   K 2007        2016        2025        2034        2043        2052
TGC TTC AGT GAA GAG AAT CAT GAA CCT CTG AGG ACT CAG TGT GCC CTT GCT GCA
 C   F   S   E   E   N   H   E   P   L   R   T   Q   C   A   L   A   A 2061        2070        2079        2088        2097        2106
TCC AAA CTT CTA AAG AAA CCT GAT CAG GGC CGA GCT GTG AGC ACC TGT GCA CAT
 S   K   L   L   K   K   P   D   Q   G   R   A   V   S   T   C   A   H 2115        2124        2133        2142        2151        2160
CTC TTC TGG TCT GGC AGA AAC ACG GAC AAA AAT GGG GAG GAG CTT CAC GGA GGC
 L   F   W   S   G   R   N   T   D   K   N   G   E   E   L   H   G   G 2169        2178        2187        2196        2205        2214
AAG AGG GTA ATG GAG TGC CTA AAA AAA GCT CTA AAA ATA GCA AAT CAG TGC ATG
 K   R   V   M   E   C   L   K   K   A   L   K   I   A   N   Q   C   M 2223        2232        2241        2250        2259        2268
GAC CCC TCT CTA CAA GTG CAG CTT TTT ATA GAA ATT CTG AAC AGA TAT ATC TAT
 D   P   S   L   Q   V   Q   L   F   I   E   I   L   N   R   Y   I   Y

FIGURE 1F
```

```
                                2277           2286           2295           2304           2313           2322
                                TTT TAT GAA AAG GAA AAT GAT GCG GTA ACA ATT CAG GTT TTA AAC CAG CTT ATC
                                 F   Y   E   K   E   N   D   A   V   T   I   Q   V   L   N   Q   L   I 2331           2340           2349           2358           2367           2376
                                CAA AAG ATT CGA GAA GAC CTC CCG AAT CTT GAA TCC AGT GAA GAA ACA GAG CAG
                                 Q   K   I   R   E   D   L   P   N   L   E   S   S   E   E   T   E   Q 2385           2394           2403           2412           2421           2430
                                ATT AAC AAA CAT TTT CAT AAC ACA CTG GAG CAT TTG CGC TTG CGG CGG GAA TCA
                                 I   N   K   H   F   H   N   T   L   E   H   L   R   L   R   R   E   S 2439           2448           2457           2466           2475           2484
                                CCA GAA TCC GAG GGG CCA ATT TAT GAA GGT CTC ATC CTT TAA AAA GGA AAT AGC
                                 P   E   S   E   G   P   I   Y   E   G   L   I   L   *

2493           2502           2511           2520           2529           2538
                                TCA CCA TAC TCC TTT CCA TGT ACA TCC AGT GAG GGT TTT ATT ACG CTA GGT TTC 2547           2556           2565           2574           2583           2592
                                CCT TCC ATA GAT TGT GCC TTT CAG AAA TGC TGA GGT AGG TTT CCC ATT TCT TAC 2601           2610           2619           2628           2637           2646
                                CTG TGA TGT GTT TTA CCC AGC ACC TCC GGA CAC TCA CCT TCA GGA CCT TAA TAA
```

FIGURE 1G

```
      2655        2664        2673        2682        2691        2700
AAT TAT TCA CTT GGT AAG TGT TCA AGT CTT TCT GAT CAC CCC AAG TAG CAT GAC 2709        2718        2727        2736        2745        2754
TGA TCT GCA ATT TAA AAT TCC TGT GAT CTG TAA AAA AAA AAA AAA AAA AAA AAA 2763        2772        2781        2790        2799        2808
AAA AAC AAA ACC CAC AAG CAC TTA TCT TGG CTA CTA ATG AAG CTC TCC TTT TTT 2817        2826        2835        2844        2853        2862
TTG TTT GTT TGT TTG CTT CAT TGT TGA TTG TGT ATT TTC TTC ATT CCT GGG GAG 2871        2880        2889        2898        2907        2916
TAC TAA CCC AAA AGC GTC TGT CTC TTG TTT TCT AGT CCA GTT TGA GAT TAA TTT 2925        2934        2943        2952        2961        2970
AGA AGA AAG GAA TAC TGT ATG TGA AAT TCA TCT TGG GCT TTC CCC TAA ATT GCA 2979        2988        2997        3006        3015        3024
AGA TAA GGC CAT GTG TAA GAT TTT CCC TAA AAC TAG AAT ATA TTA ATG CAT GTT
```

FIGURE 1H

```
        3033      3042      3051      3060      3069      3078
TGA GAA TTT TAA AGC ACC ATG GTC AAA ACC AGA AGC TAT ATT TTG CAT ATT TGG
        3087      3096      3105      3114      3123      3132
ACT CAG CCA TCC ATT AAG AAC CCA TGT TGT CCT CTG GAC ATA TTT ATC AAT ATA
        3141      3150      3159      3168      3177      3186
ATT GGG TTT TAA ATA GTA TAA AAG ACT TGT GAT CTA TAT AAT TTA TGT ATC
        3195      3204      3213      3222      3231      3240
ACC TTC ATT GTA AAT TTA GCA GGA AAT GCA TCA CAA TTA TGA TTT TTT TTT TGC

ACC AGT GA 3'
```

FIGURE 1I

```
  1  MPTTQQSPQDEQEKLLDEAIQAVKVQSFQM                  2641812
  1  MPPI-------------------------                   GI 1354050
  1  MA-YADSPEN---------AIAVIKQRTALM                 GI 854543

31  KRCLDKNKLMDALKHASNMLGELRTSMLSP                  2641812
  5  -CLESS----------------GPLCCHQRVT                GI 1354050
 22  NRCLSQHKLMESLQHTSIMLTELRNPNLSP                  GI 854543

61  KSYYELYMAISDELHYLEVYLTDEFAKGRK                  2641812
 20  MNFIWLFLMNCTTW---KVYLTDEFAKGER                  GI 1354050
 52  KKYYELYVIHFDSLTNLSTYLIENHPQNHH                  GI 854543

91  VADLYELVQYAGNIIPRLYLLITVGVVYVK                  2641812
 47  LADLYELVQYSGNIIPRLYLLITVGVVYVK                  GI 1354050
 82  LADLYELVQYTGNVVPRLYLMITVGTSYLT                  GI 854543

121  SFPQSRKDILKDLVEMCRGVQHPLRGLFLR                  2641812
 77  SFPQSRKDILKDLVEMCRGVQHPLRGLFLR                  GI 1354050
112  FNEAPKKEILKDMIEMCRGVQNPIRGLFLR                  GI 854543

151  NYLLQCTRNILPDEGEPTDEETTGDISDSM                  2641812
107  NYLLQCTRNILPDEGEPTDEETTGDISDSM                  GI 1354050
142  YYLSQRTKELLPEDDPSFNSQ---------                  GI 854543
```

| | | | |
|---|---|---|---|
| 353 | SLINLAMKCYPDRVDYVDKVLETTVE | - - - - | 2641812 |
| 310 | SLINLAMKCYPDRVDYVDKVLETTVE | - - - - | GI 1354050 |
| 341 | SVIVLSLKWYPNNFDNLNKLFELVLQKTKD | | GI 854543 |
| 379 | - - - - - - - - - - - - - - - - - IF - - | NKLNLEHI | 2641812 |
| 336 | - - - - - - - - - - - - - - - - - IF - - | NKLNLEHI | GI 1354050 |
| 371 | YGQKNISLESEHLFLVLLSFQNSKLQLTSS | | GI 854543 |
| 389 | ATSSAVS - - - - - - - KELTRLLKIPVDTYNNIL | | 2641812 |
| 346 | ATSSAVS - - - - - - - KELTRLLKIPVDTYNNIL | | GI 1354050 |
| 401 | TTAPPNSPVTSKKHFIFQLISQCQAYKNIL | | GI 854543 |
| 414 | TV - - - - - - - LKLKHFHPLFEYF - - DYESR - - K | | 2641812 |
| 371 | TV - - - - - - - LKLKHFHPLFEYF - - DYESSPGK | | GI 1354050 |
| 431 | ALQSISLQKKVVNEIIDILMDREVEEMADN | | GI 854543 |
| 435 | SMSCYVLSNVLDYNTEIVSQDQVDSIMNLV | | 2641812 |
| 394 | SMSCYVLSNVLDYNTEIVSQDQVDSIMNLV | | GI 1354050 |
| 461 | DSESKLHPPGHSAYLVIEDKLQVQRLLSIC | | GI 854543 |
| 465 | STLIQDQPDQPVEDPDPEDFADE - - - - | | 2641812 |
| 424 | STLIQDQPDQPVEDPDPEDFADE - - - - | | GI 1354050 |
| 491 | EPLHISRSGPPANVASSDTNVDEVFFNRHD | | GI 854543 |

FIGURE 2C

```
488  - - - - - - - - - - - - - - - QSLVGRFIHLLRSEDPDQQY        2641812
447  - - - - - - - - - - - - - - - QSLVGRFIHLLRSDDPDQQY        GI 1354050
521  EESWILDPIQEKLAHLIHWIMNTTSRKQT                              GI 854543

508  - - - - - - - - - - - - - - L - ILNTARKHFGAGGNQR           2641812
467  - - - - - - - - - - - - - - L - ILNTARKHFGAGGNQR           GI 1354050
551  MKNKIQFSLEAQLEILLLIKSSFIKGGIN -                            GI 854543

525  IRFTLPPLVFAAYQLAFR - - - - - - YKENSK                      2641812
484  IRFTLPPLVFAAYQLAFR - - - - - - YKENSK                      GI 1354050
580  VKYTFPAIITNFWKLMRKCRMIQEYLLKKR                             GI 854543

549  VDDKW - - - - EKKC - QKIFSFAHQTISALIK                      2641812
508  - - - - - - - - - RRYFHLPHQTISALIK                         GI 1354050
610  PDNKTLLSHYSNLLKQMFKFVSRCINDIFN                             GI 854543

574  A - - - ELAELPLRLFLQGALAAGEIGFENHE                         2641812
533  A - - - ELAELPLRLFLQGALAAGEIGFENHE                         GI 1354050
640  SCNNSCTDLILKLNLQCAILADQLQLNE -                             GI 854543

601  TVAYEFMSQAFSLYEDEISDSKAQLAAITL                             2641812
560  TVAYEFMSQAFSLYEDEISDSKAQLAAITL                             GI 1354050
668  - ISYDFFSQAFTIFEESLSDSKTQLQALIY                            GI 854543
```

HUMAN VPS35/MEM3-RELATED PROTEIN

FIELD OF THE INVENTION

This invention relates to nucleic acid and amino acid sequences of a human Vps35/Mem3-related protein and to the use of these sequences in the diagnosis, treatment, and prevention of cancer, inflammatory disorders, lysosomal storage diseases, and disorders of membrane transport.

BACKGROUND OF THE INVENTION

Vesicular transport is the general process by which proteins synthesized in the endoplasmic reticulum are transported via the Golgi network to their appropriate cellular location, either at the cell surface or within various membrane bound organelles within the cytosol. Many of the proteins involved in this complex process are conserved among all eukaryotes.

The transport pathway involves formation of a series of transport vesicles that shuttle proteins from one membrane-bound compartment to another until they reach their final destination. Sorting of proteins into the appropriate transport vesicle is mediated by specific receptors in the golgi which recognize the proteins and sequester them into transport vesicles. For example, proteins destined for the mammalian lysosome, equivalent to the yeast vacuole, are tagged in the golgi with mannose-6-phosphate (Man-6-P) moieties. This tag is recognized in the trans golgi network by Man-6-P receptors (MPRs) which mediate the sorting and transport of lysosomal proteins to an endosomal compartment. The proteins are subsequently delivered to a lysosome by an unknown mechanism.

Recognition between donor and acceptor compartments is mediated by snare proteins, complementary identifiers displayed on the surface of transport vesicles (v-snares) and their appropriate target compartments (t-snares). Following recognition between complementary snare proteins, the two membrane bound compartments fuse to complete the delivery of the protein. The receptors are then recycled back to the golgi for another round or sorting and transport. Proteins that do not carry targeting signals for delivery to an intracellular compartment, such as constitutively secreted proteins and plasma membrane proteins, instead enter a default pathway (bulk flow) in which they are sorted into vesicles that eventually fuse with the plasma membrane. (Rothman, J. E. and Wieland, F. T. et al. (1996) 727:227–33.) Components of the vacuolar protein sorting machinery have been identified in yeast through a variety of genetic selection schemes. A set of vacuolar protein sorting (vps) mutants have defined at least 45 genes that encode proteins involved in vesicular transport. One of these genes, Vps35, was identified in a selection for mutants that mislocalize and secrete a hybrid protein. This hybrid consisted of a fusion between a soluble vacuolar hydrolase, carboxypeptidase Y (CPY), and a secreted enzyme, invertase. Vps35 mutants also mislocalize and secrete endogenous CPY, but not other vacuolar proteins, e.g., proteinase A, proteinase B, and alkaline phosphatase. Vps35 mutants are viable and have morphologically normal vacuoles, indicating that they are competent in assembly of the vacuolar compartment. Thus, Vps35 mutants appear to disrupt an alternate pathway required for the sorting and/or transport of a subset of vacuolar proteins.

Mutants with a selective missorting phenotype similar to Vps35, such as Vps10, Vps29, and Vps30, define additional components of the Vps35 dependent sorting/transport pathway. Vps10 encodes a transmembrane protein that shuttles between golgi and vacuolar compartments, and functions as a receptor for soluble vacuolar hydrolases, such as CPY. Vps29, Vps30, and Vps35 encode novel hydrophilic proteins that all appear to be required for normal recycling of Vps10 receptors from the vacuole back to the golgi. Vps35 encodes a 110 kDa protein that binds directly to Vps10 and appears to associate peripherally with golgi membranes. In Vps29 or Vps30 mutants, both Vps10 and Vps35 are mislocalized to a cell fraction enriched in vacuoles. (Paravicini, G. et al. (1992) Mol. Biol. Cell 3:415–427; Marcusson et al. (1994) Cell 77:579–586; and Seaman et al. (1997) J. Cell Biol. 137:79–92.)

A mammalian gene, Mem3, which shares 33% amino acid sequence identity with Vps35, has been isolated from a library of mouse genes highly expressed in unfertilized eggs. Mem3 is also expressed at high levels during preimplantation development and at lower levels in adult tissues. This expression pattern is consistent with a proposed role for Mem3 as a housekeeping protein involved in vesicular transport. (Paravicini et al., supra; Hwang, S. -Y. Et al. (1996) Mammalian Genome 7:586–590.)

Defects in the expression or function of components of vesicular transport pathways can result in mislocalization, and consequent abnormal function, of many critical proteins, e.g., membrane receptors, transporters and other membrane proteins, neurotransmitters, hormones, and lysosomal and digestive enzymes. Thus, components of vesicular transport pathways may play a play a role in certain disorders of cell proliferation and metabolism.

The discovery of a new human Vps35/Mem3-related protein and the polynucleotides encoding it satisfies a need in the art by providing new compositions which are useful in the diagnosis, treatment, and prevention of cancer, inflammatory disorders, lysosomal storage diseases, and disorders of membrane transport.

SUMMARY OF THE INVENTION

The invention features a substantially purified polypeptide, human Vps35/Mem3-related protein (hvmrp), comprising the amino acid sequence of SEQ ID NO:1 or a fragment of SEQ ID NO:1.

The invention further provides a substantially purified variant of hvmrp having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide comprising a sequence of SEQ ID NO:2 or a fragment of SEQ ID NO:2, and an isolated and purified polynucleotide variant having at least 90% polynucleotide identity to the polynucleotide comprising SEQ ID NO:2 or a fragment of SEQ ID NO:2. The invention also provides an isolated and purified polynucleotide which is complementary to the polynucleotide comprising SEQ ID NO:2 or a fragment of SEQ ID NO:2.

The invention further provides an expression vector containing at least a fragment of the polynucleotide sequence encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding hvmrp under conditions suitable for the expression of the polypeptide; and (b) recovering the polypeptide from the host cell culture.

The invention also provides a pharmaceutical composition comprising a substantially purified hvmrp having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of a pharmaceutical composition comprising an antagonist of hvmrp.

The invention also provides a method for treating or preventing an inflammatory disorder, the method comprising administering to a subject in need of such treatment an effective amount of an antagonist of hvmrp.

The invention also provides a method for treating or preventing a lysosomal storage disease, the method comprising administering to a subject in need of such treatment an effective amount of a pharmaceutical composition comprising substantially purified hvmrp.

The invention also provides a method for treating or preventing a disorder of membrane transport, the method comprising administering to a subject in need of such treatment an effective amount of a pharmaceutical composition comprising substantially purified hvmrp.

The invention also provides a method for detecting a polynucleotide encoding hvmrp in a biological sample containing nucleic acids, the method comprising the steps of: (a) hybridizing the complement of the polynucleotide sequence encoding the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding hvmrp in the biological sample. In one aspect, the nucleic acids of the biological sample are amplified by the polymerase chain reaction prior to the hybridizing step.

BRIEF DESCRIPTION OF THE FIGURES

FIG. 1A, 1B, 1C, 1D, 1E, 1F, 1G, 1H, and 1I show the amino acid sequence (SEQ ID NO:1) and nucleic acid sequence (SEQ ID NO:2) of hvmrp. The alignment was produced using MACDNASIS PRO™ software (Hitachi Software Engineering Co. Ltd., San Bruno, Calif.).

Figure 2B:
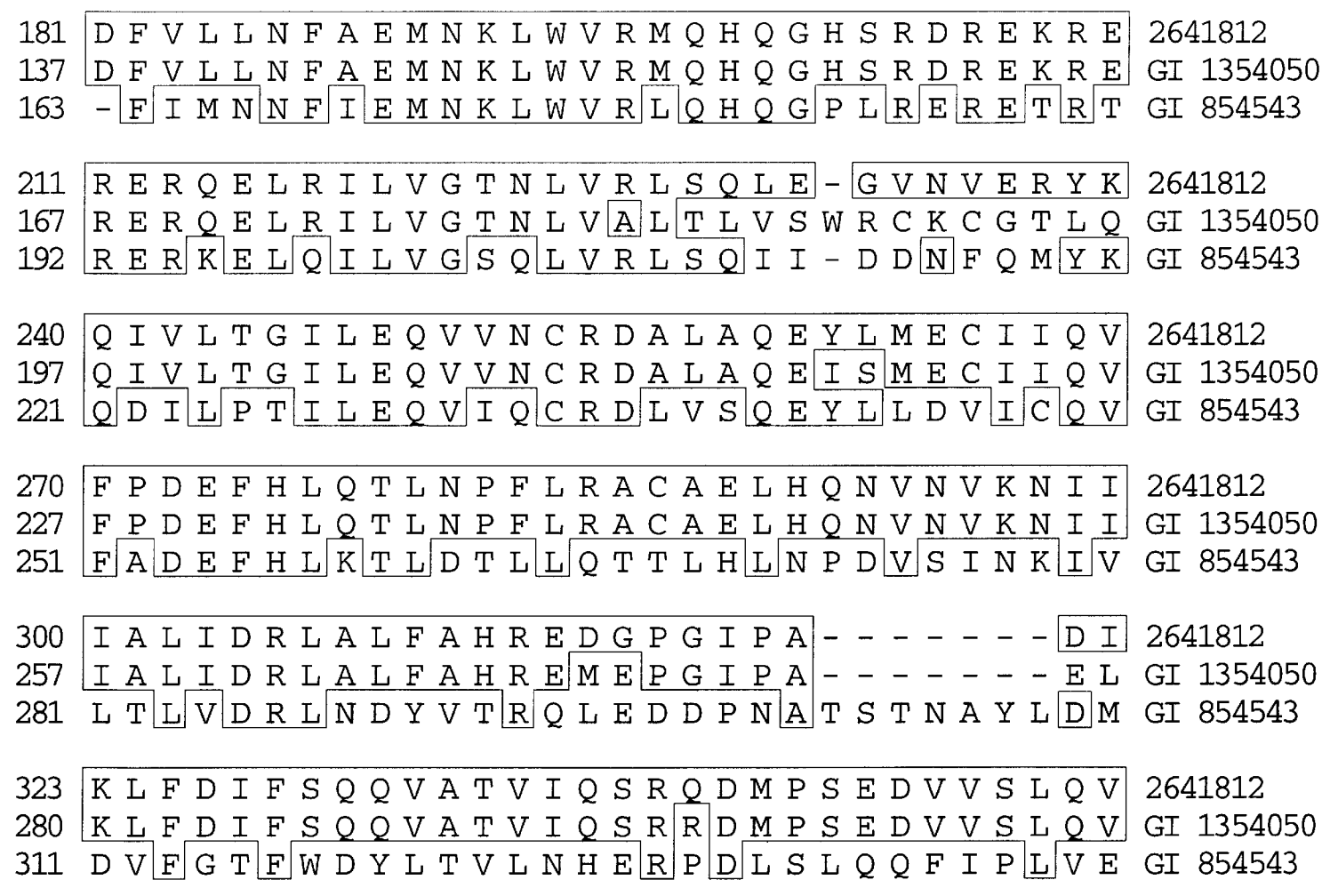
Figure 2E:
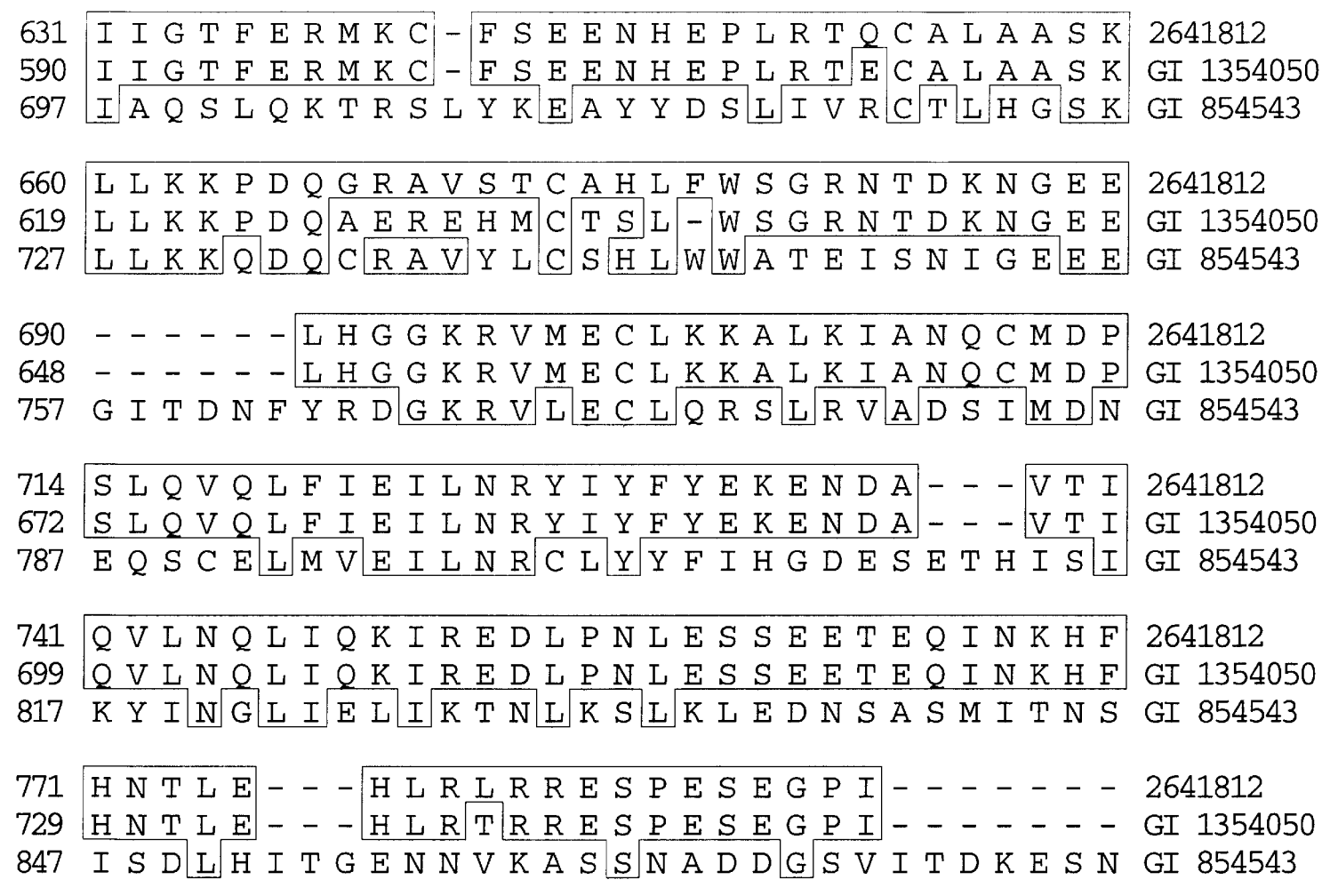
Figure 2F:
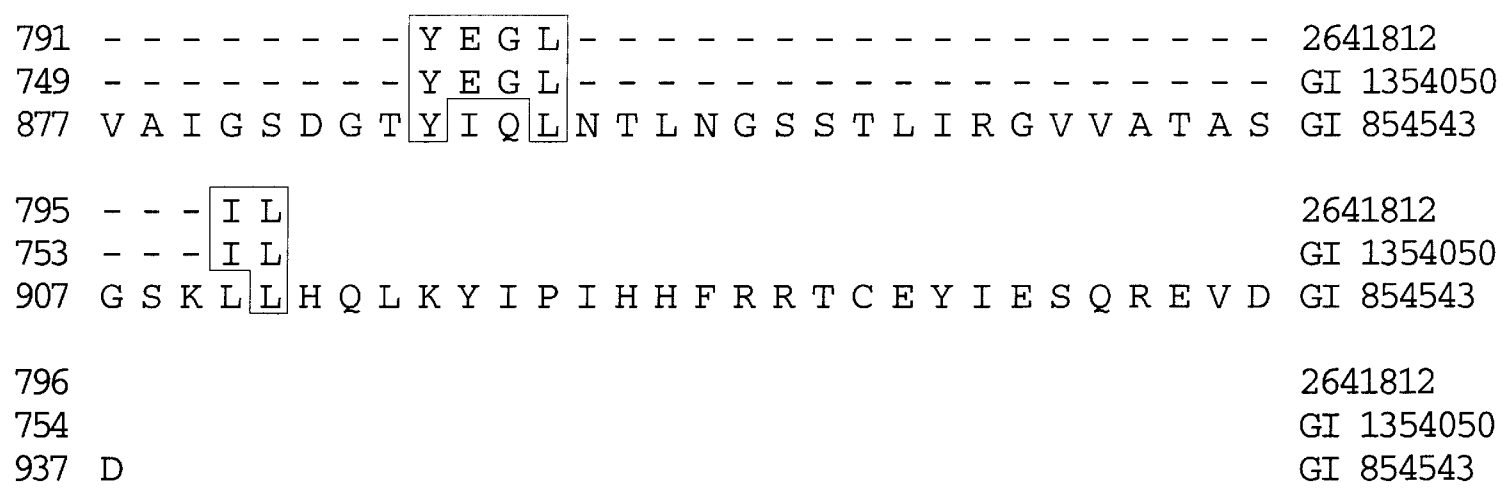

FIGS. 2A, 2B, 2C, 2D, 2E and 2F show the amino acid sequence alignments among hvmrp (2641812); SEQ ID NO:1), Mem3 (GI 1354050; SEQ ID NO:3), and Vps35 (GI 854543; SEQ ID NO:4) produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"hvmrp," as used herein, refers to the amino acid sequences of substantially purified hvmrp obtained from any species, particularly a mammalian species, including bovine, ovine, porcine, murine, equine, and preferably the human species, from any source, whether natural, synthetic, semisynthetic, or recombinant.

The term "agonist," as used herein, refers to a molecule which, when bound to hvmrp, increases or prolongs the duration of the effect of hvmrp. Agonists may include proteins, nucleic acids, carbohydrates, or any other molecules which bind to and modulate the effect of hvmrp.

An "allele" or an "allelic sequence," as these terms are used herein, is an alternative form of the gene encoding hvmrp. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding hvmrp, as described herein, include those sequences with deletions, insertions, or substitutions of different nucleotides, resulting in a polynucleotide the same hvmrp or a polypeptide with at least one functional characteristic of hvmrp. Included within this definition are polymorphisms which may or may not be readily detectable using a particular oligonucleotide probe of the polynucleotide encoding hvmrp, and improper or unexpected hybridization to alleles, with a locus other than the normal chromosomal locus for the polynucleotide sequence encoding hvmrp. The encoded protein may also be "altered," and may contain deletions, insertions, or substitutions of amino acid residues which produce a silent change and result in a functionally equivalent hvmrp. Deliberate amino acid substitutions may be made on the basis of similarity in polarity, charge, solubility, hydrophobicity, hydrophilicity, and/or the amphipathic nature of the residues, as long as the biological or immunological activity of hvmrp is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of hvmrp which are preferably about 5 to about 15 amino acids in length and which retain some biological activity or immunological activity of hvmrp. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual, pp.*1–5, Cold Spring Harbor Press, Plainview, N.Y.)

The term "antagonist," as it is used herein, refers to a molecule which, when bound to hvmrp, decreases the amount or the duration of the effect of the biological or immunological activity of hvmrp. Antagonists may include proteins, nucleic acids, carbohydrates, antibodies, or any other molecules which decrease the effect of hvmrp.

As used herein, the term "antibody" refers to intact molecules as well as to fragments thereof, such as Fab, $F(ab')_2$, and Fv fragments, which are capable of binding the epitopic determinant. Antibodies that bind hvmrp polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic hvmrp, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "a-G-T" binds to the complementary sequence "T-C-a." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

a "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding hvmrp or fragments of hvmrp may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence .

As used herein, the term "correlates with expression of a polynucleotide" indicates that the detection of the presence of nucleic acids, the same or related to a nucleic acid sequence encoding hvmrp, by northern analysis is indicative of the presence of nucleic acids encoding hvmrp in a sample, and thereby correlates with expression of the transcript from the polynucleotide encoding hvmrp.

a "deletion," as the term is used herein, refers to a change in the amino acid or nucleotide sequence that results in the absence of one or more amino acid residues or nucleotides.

The term "derivative," as used herein, refers to the chemical modification of hvmrp, of a polynucleotide sequence encoding hvmrp, or of a polynucleotide sequence complementary to a polynucleotide sequence encoding hvmrp. Chemical modifications of a polynucleotide sequence can include, for example, replacement of hydrogen by an alkyl, acyl, or amino group. a derivative polynucleotide encodes a polypeptide which retains at least one biological or immunological function of the natural molecule. a derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." a partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. a substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 10 K to 10 M in size, and which contain all of the elements required for stable mitotic chromosome segregation and maintenance. (Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. a hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of hvmrp. For example, modulation may cause an increase or a decrease in protein activity, binding characteristics, or any other biological, functional, or immunological properties of hvmrp.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.) The phrases "percent identity" or "% identity" refer to the percentage of sequence similarity found in a comparison of two or more amino acid or nucleic acid sequences. Percent identity can be determined electronically, e.g., by using the MegAlign program (Lasergene software package, DNASTAR, Inc., Madison Wis.). The MegAlign program can create alignments between two or more sequences according to different methods, e.g., the Clustal Method. (Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) Methods in Enzymology 183:626–645.) Identity between sequences can also be determined by other methods known in the art, e.g., by varying hybridization conditions.

The term "sample," as used herein, is used in its broadest sense. a biological sample suspected of containing nucleic acids encoding hvmrp, or fragments thereof, or hvmrp itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "a," the presence of a polypeptide containing the epitope a, or the presence of free unlabeled a, in a reaction containing free labeled a and the antibody will reduce the amount of labeled a that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 $\mu$g/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

a "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time. a "variant" of hvmrp, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human Vps35/Mem3-related protein (hvmrp), the polynucleotides encoding hvmrp, and the use of these compositions for the diagnosis, treatment, or prevention of cancer, inflammatory disorders, lysosomal storage diseases, and disorders of membrane transport.

Nucleic acids encoding the hvmrp of the present invention were first identified in Incyte Clone 2641812 from the cDNA library LUNGTUT08 using a computer search for amino acid sequence alignments. A consensus sequence, SEQ ID NO:2, was derived from the following overlapping and/or extended nucleic acid sequences: Incyte Clones 191756, (SYNORAB01), 2024724 (KERANOT02), 3107861 (BRSTTUT15), 1558139 (BLADTUT04), 2098732 (BRAITUT02), 3044671 (HEAANOT01), 2588772 (LUNGNOT22), 2296469 (BRSTNOT05), 2638396 (BONTNOT01), 025444 (SPLNFET01), 1985374 (LUNGAST01), 2132887 (OVARNOT03), 1805567 (SINTNOT13), 1002734 (BRSTNOT03) and 2641812 (LUNGTUT08).

In one embodiment, the invention encompasses a polypeptide comprising the amino acid sequence of SEQ ID NO:1, as shown in FIGS. 1A, 1B, 1C, 1D, 1E, 1F, 1G, 1H, and 1I. hvmrp is 796 amino acids in length and has two potential amidation sites at $K_{87}$ and $G_{692}$; one potential cAMP- and cGMP-dependent protein kinase phosphorylation site at residue $S_{783}$; eleven potential casein kinase II phosphorylation sites at residues $S_7$, $S_{62}$, $S_{125}$, $T_{168}$, $T_{172}$, $S_{228}$, $S_{338}$, $T_{375}$, $S_{547}$, $S_{612}$, and $S_{759}$; six potential protein kinase C phosphorylation sites at residues $S_{59}$, $S_{125}$, $S_{432}$, $T_{512}$, $S_{679}$, and $T_{683}$; and one potential tyrosine phosphorylation site at $Y_{368}$. As shown in FIG. 2A, 2B, and 2C, hvmrp has chemical and structural homology with mouse Mem3 (GI 1354050; SEQ ID NO:3) and with yeast Vps35 (GI 854543). In particular, hvmrp shares 87% identity with mouse Mem3 and 31% identity with yeast Vps35. The C-terminal region of hvmrp is most conserved with mouse Mem3 (92% identity between residues 78 to 796 of hvmrp and residues 34 to 754 of Mem3). However, the two proteins diverge significantly at the N-terminus (11% identity between residues 1 to 78 of hvmrp and residues 1 to 34 of Mem3). This region of hvmrp is significantly more similar to the N-terminus of the yeast protein (45% identity between residues 1 to 78 of hvmrp and residues 1 to 69 of yeast Vps35). Northern analysis shows the expression of this sequence in reproductive, nervous, cardiovascular, and gastrointestinal cDNA libraries, at least 48% of which are associated with neoplastic disorders, and at least 25% with immune response.

The invention also encompasses hvmrp variants. A preferred hvmrp variant is one which has at least about 80%, more preferably at least about 90%, and most preferably at least about 95% amino acid sequence identity to the hvmrp amino acid sequence, and which contains at least one functional or structural characteristic of hvmrp.

The invention also encompasses polynucleotides which encode hvmrp. In a particular embodiment, the invention encompasses a polynucleotide sequence comprising the sequence of SEQ ID NO:2, which encodes an hvmrp.

The invention also encompasses a variant of a polynucleotide sequence encoding hvmrp. In particular, such a variant polynucleotide sequence will have at least about 80%, more preferably at least about 90%, and most preferably at least about 95% polynucleotide sequence identity to the polynucleotide sequence encoding hvmrp. a particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of hvmrp.

It will be appreciated by those skilled in the art that as a result of the degeneracy of the genetic code, a multitude of polynucleotide sequences encoding hvmrp, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring hvmrp, and all such variations are to be considered as being specifically disclosed.

Although nucleotide sequences which encode hvmrp and its variants are preferably capable of hybridizing to the nucleotide sequence of the naturally occurring hvmrp under appropriately selected conditions of stringency, it may be advantageous to produce nucleotide sequences encoding hvmrp or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding hvmrp and its derivatives without altering the encoded amino acid sequences include the production of RNA transcripts having more desirable properties, such as a greater half-life, than transcripts produced from the naturally occurring sequence.

The invention also encompasses production of DNA sequences which encode hvmrp and hvmrp derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding hvmrp or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by GIBCO/BRL (Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding hvmrp may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode hvmrp may be used in recombinant DNA molecules to direct expression of hvmrp, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express hvmrp.

As will be understood by those of skill in the art, it may be advantageous to produce hvmrp-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter hvmrp encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding hvmrp may be ligated to a heterologous sequence to encode a fusion protein. For example, to screen peptide libraries for inhibitors of hvmrp activity, it may be useful to encode a chimeric hvmrp protein that can be recognized by a commercially available antibody. a fusion protein may also be engineered to contain a cleavage site located between the hvmrp encoding sequence and the heterologous protein sequence, so that hvmrp may be cleaved and purified away from the heterologous moiety.

In another embodiment, sequences encoding hvmrp may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of hvmrp, or a fragment thereof. For example, peptide synthesis can be performed using various solid-phase techniques (Roberge, J. Y. et al. (1995) Science 269:202–204) and automated synthesis may be achieved using the ABI 431 A Peptide Synthesizer (Perkin Elmer).

The newly synthesized peptide may be substantially purified by preparative high performance liquid chromatography. (See, e.g., Chiez, R. M. and Regnier, F. Z. (1990) Methods Enzymol. 182:392–421.). The composition of the synthetic peptides may be confirmed by amino acid analysis or by sequencing. (See, e.g., the Edman degradation procedure described in Creighton, T. (1983) *Proteins, Structures and Molecular Principles*, WH Freeman and Co., New York, N.Y.). Additionally, the amino acid sequence of hvmrp, or any part thereof, may be altered during direct synthesis and/or combined with sequences from other proteins, or any part thereof, to produce a variant polypeptide.

In order to express a biologically active hvmrp, the nucleotide sequences encoding hvmrp or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding hvmrp and appropriate transcriptional and translational control elements. These methods include in vitro recombinant DNA techniques, synthetic techniques, and in vivo genetic recombination known in the art. (See, e.g., Sambrook, J. et al. (1989) *Molecular Cloning, a Laboratory Manual*, ch. 4, 8, and 16–17, Cold Spring Harbor Press, Plainview, N.Y.; and Ausubel, F. M. et al. (1995 and periodic supplements) *Current Protocols in Molecular Biology*, ch. 9, 13, and 16, John Wiley & Sons, New York, N.Y.)

a variety of expression vector/host systems may be utilized to contain and express sequences encoding hvmrp. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems.

The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or pSport1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding hvmrp, vectors based on SV40 or EBV may be used with an appropriate selectable marker.

In bacterial systems, a number of expression vectors may be selected depending upon the use intended for hvmrp. For example, when large quantities of hvmrp are needed for the induction of antibodies, vectors which direct high level expression of fusion proteins that are readily purified may be used. Such vectors include, but are not limited to, multi-functional E. coli cloning and expression vectors such as BLUESCRIPT (Stratagene), in which the sequence encoding hvmrp may be ligated into the vector in frame with sequences for the amino-terminal Met and the subsequent 7 residues of β-galactosidase so that a hybrid protein is produced, pIN vectors (Van Heeke, G. and S.M. Schuster (1989) J. Biol. Chem. 264:5503–5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding hvmrp may be driven by any of a number of promoters. For example, viral promoters such as the 35S and 19S promoters of CaMV may be used alone or in combination with the omega leader sequence from TMV. (Takamatsu, N. (1987) EMBO J. 6:307–31 1.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express hvmrp. For example, in one such system, *Autographa californica* nuclear polyhedrosis virus (AcNPV) is used as a vector to express foreign genes in *Spodoptera frugiperda* cells or in Trichoplusia larvae. The sequences encoding hvmrp may be cloned into a non-essential region of the virus, such as the polyhedrin gene, and placed under control of the polyhedrin promoter. Successful insertion of hvmrp will render the polyhedrin gene inactive and produce recombinant virus lacking coat protein. The recombinant viruses may then be used to infect, for example, *S. frugiperda* cells or Trichoplusia larvae in which hvmrp may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding hvmrp may be ligated into an adenovirus transcription/translation complex consisting of the late promoter and tripartite leader sequence. Insertion in a non-essential E1 or E3 region of the viral genome may be used to obtain a viable virus which is capable of expressing hvmrp in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 Mb to 10 Mb are constructed and delivered via conventional delivery methods (liposomes, polycationic amino polymers, or vesicles) for therapeutic purposes.

Specific initiation signals may also be used to achieve more efficient translation of sequences encoding hvmrp. Such signals include the ATG initiation codon and adjacent sequences. In cases where sequences encoding hvmrp and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing hvmrp can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyl-transferase genes (Lowy, I. et al. (1980) Cell 22:817–23), which can be employed in tk⁻ or apr⁻ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding hvmrp is inserted within a marker gene sequence, transformed cells containing sequences encoding hvmrp can be identified by the absence of marker gene function. Alternatively, a marker gene can be placed in tandem with a sequence encoding hvmrp under the control of a single promoter. Expression of the marker gene in response to induction or selection usually indicates expression of the tandem gene as well.

Alternatively, host cells which contain the nucleic acid sequence encoding hvmrp and express hvmrp may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein sequences.

The presence of polynucleotide sequences encoding hvmrp can be detected by DNA—DNA or DNA-RNA hybridization or amplification using probes or fragments or fragments of polynucleotides encoding hvmrp. Nucleic acid amplification based assays involve the use of oligonucleotides or oligomers based on the sequences encoding hvmrp to detect transformants containing DNA or RNA encoding hvmrp. a variety of protocols for detecting and measuring the expression of hvmrp, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). a two-site, monoclonal-based immunoassay utilizing monoclonal antibodies reactive to two non-interfering epitopes on hvmrp is preferred, but a competitive binding assay may be employed. (See, e.g., Hampton, R. et al. (1990) *Serological Methods, a Laboratory Manual*, Section IV, APS Press, St Paul, Minn.; and Maddox, D. E. et al. (1983) J. Exp. Med. 158:1211–1216.)

a wide variety of labels and conjugation techniques are known by those skilled in the art and may be used in various nucleic acid and amino acid assays. Means for producing labeled hybridization or PCR probes for detecting sequences related to polynucleotides encoding hvmrp include oligolabeling, nick translation, end-labeling, or PCR amplification using a labeled nucleotide. Alternatively, the sequences encoding hvmrp, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding hvmrp may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode hvmrp may be designed to contain signal sequences which direct secretion of hvmrp through a prokaryotic or eukaryotic cell membrane. Other constructions may be used to join sequences encoding hvmrp to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein a domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, CA), between the purification domain and the hvmrp encoding sequence may be used to facilitate purification. One such expression vector provides for expression of a fusion protein containing hvmrp and a nucleic acid encoding 6 histidine residues preceding a thioredoxin or an enterokinase cleavage site. The histidine residues facilitate purification on immobilized metal ion affinity chromatography (IMIAC)(see, e.g., Porath, J. et al. (1992) Prot. Exp. Purif. 3: 263–281), while the enterokinase cleavage site provides a means for purifying hvmrp from the fusion protein. (See e.g., Kroll, D. J. et al. (1993) DNA Cell Biol. 12:441–453.) Fragments of hvmrp may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431 A Peptide Synthesizer (Perkin Elmer). Various fragments of hvmrp may be synthesized separately and then combined to produce the full length molecule.

Therapeutics

Chemical and structural homology exists between hvmrp and Mcm3 from mouse (GI 1354050) and Vps35 from yeast (GI 854542). In addition, hvmrp is expressed in libraries derived from cancerous, inflamed, and fetal/proliferative cells and tissues. Therefore, hvmrp may play a role in cancer, inflammatory disorders, lysosomal storage diseases, and disorders of membrane transport.

Therefore, in one embodiment, an antagonist of hvmrp may be administered to a subject to treat or prevent a cancer. Such cancers can include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds hvmrp may be used directly as an antagonist or indirectly as a targeting or delivery mechanism for bringing a pharmaceutical agent to cells or tissue which express hvmrp.

In another embodiment, a vector expressing the complement of the polynucleotide encoding hvmrp may be administered to a subject to treat or prevent a cancer, including, but not limited to, those described above.

In a further embodiment, an antagonist of hvmrp may be administered to a subject to treat or prevent an inflammatory disorder. Such inflammatory disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus crythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In an additional embodiment, a vector expressing the complement of the polynucleotide encoding hvmrp may be administered to a subject to treat or prevent an inflammatory disorder, including, but not limited to, those described above.

In another embodiment, hvmrp or a fragment or derivative thereof may be administered to a subject to treat or prevent a lysosomal storage disease. Such diseases can include, but are not limited to, $G_{MI}$ gangliosidosis, Tay-Sachs disease, Sandhoff disease, Krabbe disease, Niemann-Pick disease, Gaucher disease, Fabry disease, Hurler syndrome, Morquio syndrome, Pompe disease, and Hunter syndrome.

In another embodiment, a vector capable of expressing hvmrp or a fragment or derivative thereof may be administered to a subject to treat or prevent a lysosomal storage disease including, but not limited to, those described above.

In a further embodiment, a pharmaceutical composition comprising a substantially purified hvmrp in conjunction with a suitable pharmaceutical carrier may be administered to a subject to treat or prevent a lysosomal storage disease including, but not limited to, those provided above.

In still another embodiment, an agonist which modulates the activity of hvmrp may be administered to a subject to treat or prevent a lysosomal storage disease including, but not limited to, those listed above.

In another embodiment, hvmrp or a fragment or derivative thereof may be administered to a subject to treat or prevent a disorder of membrane transport. Such disorders can include, but are not limited to, cystinuria, lysinuria, Hartnup disease, histidinuria, renal glycosuria, familial hypercholesterolemia, lethal diarrhea, juvenile pernicious anemia, and sialic acid storage disorder.

In another embodiment, a vector capable of expressing hvmrp or a fragment or derivative thereof may be administered to a subject to treat or prevent a disorder of membrane transport including, but not limited to, those described above.

In a further embodiment, a pharmaceutical composition comprising a substantially purified hvmrp in conjunction with a suitable pharmaceutical carrier may be administered to a subject to treat or prevent a disorder of membrane transport including, but not limited to, those provided above.

In still another embodiment, an agonist which modulates the activity of hvmrp may be administered to a subject to treat or prevent a disorder of membrane transport including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of hvmrp may be produced using methods which are generally known in the art. In particular, purified hvmrp may be used to produce antibodies or to screen libraries of pharmaceutical agents to identify those which specifically bind hvmrp. Antibodies to hvmrp may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with hvmrp or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to hvmrp have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of hvmrp amino acids may be fused with those of another protein, such as KLH, and antibodies to the chimeric molecule may be produced. Monoclonal antibodies to hvmrp may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. lo 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce hvmrp-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.)

Antibody fragments which contain specific binding sites for hvmrp may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between hvmrp and its specific antibody. a two-site, monoclonal-based immunoassay utilizing monoclonal antibodies reactive to two non-interfering hvmrp epitopes is preferred, but a competitive binding assay may also be employed. (Maddox, supra.)

In another embodiment of the invention, the polynucleotides encoding hvmrp, or any fragment or complement thereof, may be used for therapeutic purposes. In one aspect, the complement of the polynucleotide encoding hvmrp may be used in situations in which it would be desirable to block the transcription of the mRNA. In particular, cells may be transformed with sequences complementary to polynucleotides encoding hvmrp. Thus, complementary molecules or fragments may be used to modulate hvmrp activity, or to achieve regulation of gene function. Such technology is now well known in the art, and sense or antisense oligonucleotides or larger fragments can be designed from various locations along the coding or control regions of sequences encoding hvmrp.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding hvmrp. These techniques are described, for example, in Sambrook (supra) and in Ausubel (supra).

Genes encoding hvmrp can be turned off by transforming a cell or tissue with expression vectors which express high levels of a polynucleotide or fragment thereof encoding hvmrp. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding hvmrp. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, Molecular and Immunologic Approaches, pp. 163–177, Futura Publishing Co., Mt. Kisco, N.Y.) a complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding hvmrp.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding hvmrp. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of hvmrp, antibodies to hvmrp, and mimetics, agonists, antagonists, or inhibitors of hvmrp. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of hvmrp, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and a therapeutically effective dose refers to that amount of active ingredient, for example hvmrp or fragments thereof, antibodies of hvmrp, and agonists, antagonists or inhibitors of hvmrp, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio between therapeutic and toxic effects is the therapeutic index, which can be expressed as the LD50ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind hvmrp may be used for the diagnosis of disorders characterized by expression of hvmrp, or in assays to monitor patients being treated with hvmrp or agonists, antagonists, and inhibitors of hvmrp. Antibodies useful for diagnostic purposes may be prepared in the same manner as those described above for therapeutics. Diagnostic assays for hvmrp include methods which utilize the antibody and a label to detect hvmrp in human body fluids or in extracts of cells or tissues. The antibodies may be used with or without modification, and may be labeled by covalent or non-covalent joining with a reporter molecule. a wide variety of reporter molecules, several of which are described above, are known in the art and may be used.

a variety of protocols for measuring hvmrp, including ELISAs, RIAs, and FACS, are known in the art and provide a basis for diagnosing altered or abnormal levels of hvmrp expression. Normal or standard values for hvmrp expression are established by combining body fluids or cell extracts taken from normal mammalian subjects, preferably human, with antibody to hvmrp under conditions suitable for complex formation The amount of standard complex formation may be quantified by various methods, preferably by photometric means. Quantities of hvmrp expressed in subject, control, and disease samples from biopsied tissues are compared with the standard values. Deviation between standard and subject values establishes the parameters for diagnosing disease.

In another embodiment of the invention, the polynucleotides encoding hvmrp may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of hvmrp may be correlated with disease. The diagnostic assay may be used to distinguish between absence, presence, and excess expression of hvmrp, and to monitor regulation of hvmrp levels during therapeutic intervention.

In one aspect, hybridization with PCR probes which are capable of detecting polynucleotide sequences, including genomic sequences, encoding hvmrp or closely related molecules may be used to identify nucleic acid sequences which encode hvmrp. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding hvmrp, alleles, or related sequences.

Probes may also be used for the detection of related sequences, and should preferably contain at least 50% of the nucleotides from any of the hvmrp encoding sequences. The hybridization probes of the subject invention may be DNA or RNA and may be derived from the sequence of SEQ ID NO:2 or from genomic sequences including promoter and enhancer elements and introns of the naturally occurring hvmrp.

Means for producing specific hybridization probes for DNAs encoding hvmrp include the cloning of polynucleotide sequences encoding hvmrp or hvmrp derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding hvmrp may be used for the diagnosis of a disorder associated with expression of hvmrp. Examples of such a disorder include, but are not limited to, cancers, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders, such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis ,bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma; lysosomal storage diseases, such as $G_{MI}$ gangliosidosis, Tay-Sachs disease, Sandhoff disease, Krabbe disease, Niemann-Pick disease, Gaucher disease, Fabry disease, Hurler syndrome, Morquio syndrome, Pompe disease, and Hunter syndrome; and disorders of membrane transport, such as cystinuria, lysinuria, Hartnup disease, histidinuria, renal glycosuria, familial hypercholesterolemia, lethal diarrhea, juvenile pernicious anemia, and sialic acid storage disorder. The polynucleotide sequences encoding hvmrp may be used in Southern or northern analysis, dot blot, or other membrane-based technologies; in PCR technologies; in dipstick, pin, and ELISA assays; and in microarrays utilizing fluids or tissues from patient biopsies to detect altered hvmrp expression. Such qualitative or quantitative methods are well known in the art.

In a particular aspect, the nucleotide sequences encoding hvmrp may be useful in assays that detect the presence of associated disorders, particularly those mentioned above. The nucleotide sequences encoding hvmrp may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding hvmrp in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of hvmrp, a normal or standard profile for expression is established. This may be accomplished by combining body fluids or cell extracts taken from normal subjects, either animal or human, with a sequence, or a fragment thereof, encoding hvmrp, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the sequences encoding hvmrp may involve the use of PCR. These oligomers may be chemically synthesized, generated enzymatically, or produced in vitro. Oligomers will preferably contain a fragment of a polynucleotide encoding hvmrp, or a fragment of a polynucleotide complementary to the polynucleotide encoding hvmrp, and will be employed under optimized conditions for identification of a specific gene or condition. Oligomers may also be employed under less stringent conditions for detection or quantitation of closely related DNA or RNA sequences.

Methods which may also be used to quantitate the expression of hvmrp include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251 116 (Baldeschweiler et al.). In another aspect, a grid array analogous to a dot or slot blot (HYBRIDOT apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including BRINKMANN multi-channel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. a detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.) In another embodiment of the invention, nucleic acid sequences encoding hvmrp may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial PI constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described, e.g., in Heinz-Ulrich, et al. (1995) in Meyers, R. A. (ed.) Molecular Biology and Biotechnology, pp. 965–968, VCH Publishers New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding hvmrp on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, hvmrp, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between hvmrp and the agent being tested may be measured.

Another technique for drug screening which may be used provides for high throughput screening of compounds having suitable binding affinity to the protein of interest as described in published PCT application WO84/03564 (Geysen, et al.). In this method, large numbers of different small test compounds are synthesized on a solid substrate, such as plastic pins or some other surface. The test compounds are reacted with hvmrp, or fragments thereof, and washed. Bound hvmrp is then detected by methods well known in the art. Purified hvmrp can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding hvmrp specifically compete with a test compound for binding hvmrp. In this manner, antibodies can be used to detect the presence of any peptide which shares one or more antigenic determinants with hvmrp.

In additional embodiments, the nucleotide sequences which encode hvmrp may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. LUNGTUT08 cDNA Library Construction

The LUNGTUT08 cDNA library was constructed from lung tumor tissue obtained from a 63 year-old male. Pathology indicated a grade 3 (of 4) adenocarcinoma forming a mass penetrating the pleura of the right upper lung lobe. The five intrapulmonary peribronchial lymph nodes were negative for tumor. The bronchial margin of the resection was free of tumor. The tissue from the superior segment of the right lower lobe lung showed multiple (2) calcified granulomas. Multiple superior (1 right lower paratracheal, 4 right tracheobronchial) and inferior (10 subcarinal, 1 right inferior pulmonary ligament) mediastinal and N1 (2 right interlobar, 1 right lobar) lymph nodes were negative for tumor. In addition, budding yeast forms resembling histoplasma were identified in two lymph nodes stained with GMS (silver). Patient history included atherosclerotic coronary artery disease, an episode of acute myocardial infarction, neoplasm of the rectum, tobacco abuse and cardiac dysrhythmia. Family history included a malignant stomach neoplasm in the father; a malignant upper lung lobe neoplasm, diabetes type II, atherosclerotic coronary artery disease and an episode of acute myocardial infarction in siblings; and congestive heart failure in the mother.

The frozen tissues were homogenized and lysed in Trizol reagent (1 gm tissue/10 ml Trizol; Catalog #10296-028; Gibco/BRL), a monoplastic solution of phenol and guanidine isothiocyanate, using a POLYTRON PT-3000 homogenizer (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. The RNA was re-extracted twice with acid phenol-chloroform pH 4.7 and precipitated using 0.3M sodium acetate and 2.5 volumes ethanol. The mRNA was then isolated using the OLIGOTEX kit (QIAGEN, Inc., Chatsworth, Calif.) and used to construct the cDNA library.

The mRNA was handled according to the recommended protocols in the SUPERSCRIPT plasmid system for cDNA synthesis and plasmid cloning (Catalog #18248-013, Gibco/BRL). The cDNAs were fractionated on a SEPHAROSE CL4B column (Catalog #275105-01; Pharmacia), and those cDNAs exceeding 400 bp were ligated into pINCY 1. The plasmid pINCY 1 was subsequently transformed into DH5a competent cells (Catalog #18258-012; Gibco/BRL).

II Isolation and Sequencing of cDNA Clones

Plasmid DNA was released from the cells and purified using the R.E.A.L. Prep 96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from MJ Research, Watertown, Mass.) and Applied Biosystems 377 DNA sequencing systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S.F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than a, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra, ch. 7) and Ausubel, F. M. et al. (supra, ch. 4 and 16).

Analogous computer techniques applying BLAST are used to search for identical or related molecules in nucleotide databases such as GenBank or the LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding hvmrp occurs. Abundance and percent abundance are also reported. Abundance directly reflects the number of times a particular transcript is represented in a cDNA library, and percent abundance is abundance divided by the total number of sequences examined in the cDNA library.

V. Extension of hvmrp Encoding Polynucleotides

The nucleic acid sequence of Incyte Clone 2641812 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to 5 the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region. to High fidelity amplification was obtained by following the instructions for the XL-PCR kit (Perkin Elmer) and thoroughly mixing the enzyme and reaction mix. PCR was performed using the Peltier thermal cycler (PTC200; M.J. Research, Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) | a 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (Sambrook, supra, Appendix a, p. 2.). After incubation for one hour at 37° C., the E. coli mixture was plated on Luria Bertani (LB) agar (Sambrook, supra, Appendix a, p. 1) containing 2× Carb. The following day, several colonies were randomly picked from each plate and cultured in 150 µl of liquid LB/2× Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer and 250 µCi of [γ-$^{32}$P] adenosine triphosphate (Amersham) and T4 polynucleotide kinase (DuPont NEN, Boston, Mass.). The labeled oligonucleotides are substantially purified using a SEPHADEX G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN®).

The DNA from each digest is fractionated on a 0.7 percent agarose gel and transferred to nylon membranes (NYTRAN Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots or the blots are exposed to in a Phosphoimager cassette (Molecular Dynamics, Sunnyvale, Calif.), hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). a matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra).

In the alternative, a chemical coupling procedure and an ink jet device are used to synthesize oligomers on the surface of a substrate. (See Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. a typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequences complementary to the hvmrp-encoding sequences, or any parts thereof, are used to detect, decrease, or inhibit expression of naturally occurring hvmrp. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of hvmrp.

To inhibit transcription, a complementary oligonucleotide is designed from the most unique 5' sequence and used to prevent promoter binding to the coding sequence. To inhibit translation, a complementary oligonucleotide is designed to prevent ribosomal binding to the hvmrp-encoding transcript.

IX. Expression of hvmrp

Expression of hvmrp is accomplished by subcloning the cDNAs into appropriate vectors and transforming the vectors into host cells. In this case, the cloning vector is also used to express hvmrp in *E. coli*. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of hvmrp into bacterial growth media which can be used directly in the following assay for activity.

X. Demonstration of hvmrp Activity hvmrp activity can be demonstrated using a plate assay for invertase activity, similar to that described by Seaman et al. (supra.). This plate assay is used to assess the ability of hvmrp to restore intracellular localization of a CPY-Invertase fusion protein (CPY-Inv) in a Vps35 mutant cell line. Sequences encoding hvmrp, along with a selectable marker, LEU, are expressed from a construct introduced into SEY35-17 cells (Vps35-17, leu 2-3, 112) which also carry a plasmid encoding the CPY-Inv fusion protein (pCPY-50). Yeast expression vectors are commercially available, and the techniques to introduce them into cells are well known to those skilled in the art. Leu$^+$ transformants are selected and replica plated onto selective SM fructose medium and incubated overnight at 26° C. An invertase assay solution containing 125 mM sucrose, 100 mM sodium acetate (pH 5.5), 10 μg/ml horseradish peroxidase, 8 units/ml glucose oxidase, 2 mM O-dianisidine is mixed with as equal volume of a 2.4% agar solution (at 50° C.) and poured over the replica colonies. After five minutes at room temperature, colonies that secrete the CPY-Inv fusion turn red, due to a color reaction caused by secretion of the CPY-Inv fusion into the medium. The intensity of the color reaction is proportional to the amount of invertase activity in the medium. Colonies that localize CPY-Inv to an intracellular compartment remain white. SEY35-17 colonies carrying both the hvmrp and the CPY-Inv fusion expression constructs remain white whereas control colonies (without the hvmrp expression construct) turn red.

XI. Production of hvmrp Specific Antibodies hvmrp substantially purified using PAGE electrophoresis (Harrington, M. G. (1990) Methods Enzymol. 182:488–495), or other purification techniques, is used to immunize rabbits and to produce antibodies using standard protocols. The hvmrp amino acid sequence is analyzed using DNASTAR software (DNASTAR Inc) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel F. M. et al. (1995 and periodic supplements) *Current Protocols in Molecular Biology*, ch. 11, John Wiley & Sons, New York, N.Y. and by others.

Typically, the oligopeptides are 15 residues in length, and are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring hvmrp Using Specific Antibodies

Naturally occurring or recombinant hvmrp is substantially purified by immunoaffinity chromatography using antibodies specific for hvmrp. An immunoaffinity column is constructed by covalently coupling hvmrp antibody to an activated chromatographic resin, such as CNBr-activated SEPHAROSE (Pharmacia & Upjohn). After the coupling, the resin is blocked and washed according to the manufacturer's instructions.

Media containing hvmrp are passed over the immunoaffinity column, and the column is washed under conditions that allow the preferential absorbance of hvmrp (e.g., high -continued Leu Trp Val Arg Met Gln His Gln Gly His Ser Arg Asp Arg Glu Lys
          195                 200                 205

Arg Glu Arg Glu Arg Gln Glu Leu Arg Ile Leu Val Gly Thr Asn Leu
    210                 215                 220

Val Arg Leu Ser Gln Leu Glu Gly Val Asn Val Glu Arg Tyr Lys Gln
225                 230                 235                 240

Ile Val Leu Thr Gly Ile Leu Glu Gln Val Val Asn Cys Arg Asp Ala
                245                 250                 255

Leu Ala Gln Glu Tyr Leu Met Glu Cys Ile Ile Gln Val Phe Pro Asp
            260                 265                 270

Glu Phe His Leu Gln Thr Leu Asn Pro Phe Leu Arg Ala Cys Ala Glu
        275                 280                 285

Leu His Gln Asn Val Asn Val Lys Asn Ile Ile Ile Ala Leu Ile Asp
    290                 295                 300

Arg Leu Ala Leu Phe Ala His Arg Glu Asp Gly Pro Gly Ile Pro Ala
305                 310                 315                 320

Asp Ile Lys Leu Phe Asp Ile Phe Ser Gln Gln Val Ala Thr Val Ile
                325                 330                 335

Gln Ser Arg Gln Asp Met Pro Ser Glu Asp Val Val Ser Leu Gln Val
            340                 345                 350

Ser Leu Ile Asn Leu Ala Met Lys Cys Tyr Pro Asp Arg Val Asp Tyr
        355                 360                 365

Val Asp Lys Val Leu Glu Thr Thr Val Glu Ile Phe Asn Lys Leu Asn
    370                 375                 380

Leu Glu His Ile Ala Thr Ser Ser Ala Val Ser Lys Glu Leu Thr Arg
385                 390                 395                 400

Leu Leu Lys Ile Pro Val Asp Thr Tyr Asn Asn Ile Leu Thr Val Leu
                405                 410                 415

Lys Leu Lys His Phe His Pro Leu Phe Glu Tyr Phe Asp Tyr Glu Ser
            420                 425                 430

Arg Lys Ser Met Ser Cys Tyr Val Leu Ser Asn Val Leu Asp Tyr Asn
        435                 440                 445

Thr Glu Ile Val Ser Gln Asp Gln Val Asp Ser Ile Met Asn Leu Val
    450                 455                 460

Ser Thr Leu Ile Gln Asp Gln Pro Asp Gln Pro Val Glu Asp Pro Asp
465                 470                 475                 480

Pro Glu Asp Phe Ala Asp Glu Gln Ser Leu Val Gly Arg Phe Ile His
                485                 490                 495

Leu Leu Arg Ser Glu Asp Pro Asp Gln Gln Tyr Leu Ile Leu Asn Thr
            500                 505                 510

Ala Arg Lys His Phe Gly Ala Gly Gly Asn Gln Arg Ile Arg Phe Thr
        515                 520                 525

Leu Pro Pro Leu Val Phe Ala Ala Tyr Gln Leu Ala Phe Arg Tyr Lys
    530                 535                 540

Glu Asn Ser Lys Val Asp Asp Lys Trp Glu Lys Lys Cys Gln Lys Ile
545                 550                 555                 560

Phe Ser Phe Ala His Gln Thr Ile Ser Ala Leu Ile Lys Ala Glu Leu
                565                 570                 575

Ala Glu Leu Pro Leu Arg Leu Phe Leu Gln Gly Ala Leu Ala Ala Gly
            580                 585                 590

Glu Ile Gly Phe Glu Asn His Glu Thr Val Ala Tyr Glu Phe Met Ser
        595                 600                 605

```
Gln Ala Phe Ser Leu Tyr Glu Asp Glu Ile Ser Asp Ser Lys Ala Gln
            610                 615                 620

Leu Ala Ala Ile Thr Leu Ile Ile Gly Thr Phe Glu Arg Met Lys Cys
625                 630                 635                 640

Phe Ser Glu Glu Asn His Glu Pro Leu Arg Thr Gln Cys Ala Leu Ala
                    645                 650                 655

Ala Ser Lys Leu Leu Lys Pro Asp Gln Gly Arg Ala Val Ser Thr
                660                 665                 670

Cys Ala His Leu Phe Trp Ser Gly Arg Asn Thr Asp Lys Asn Gly Glu
            675                 680                 685

Glu Leu His Gly Gly Lys Arg Val Met Glu Cys Leu Lys Lys Ala Leu
        690                 695                 700

Lys Ile Ala Asn Gln Cys Met Asp Pro Ser Leu Gln Val Gln Leu Phe
705                 710                 715                 720

Ile Glu Ile Leu Asn Arg Tyr Ile Tyr Phe Tyr Glu Lys Glu Asn Asp
                725                 730                 735

Ala Val Thr Ile Gln Val Leu Asn Gln Leu Ile Gln Lys Ile Arg Glu
                740                 745                 750

Asp Leu Pro Asn Leu Glu Ser Ser Glu Glu Thr Glu Gln Ile Asn Lys
            755                 760                 765

His Phe His Asn Thr Leu Glu His Leu Arg Leu Arg Arg Glu Ser Pro
        770                 775                 780

Glu Ser Glu Gly Pro Ile Tyr Glu Gly Leu Ile Leu
785                 790                 795

(2) INFORMATION FOR SEQ ID NO:2:

(i) SEQUENCE CHARACTERISTICS:
        (A) LENGTH: 3246 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT08
        (B) CLONE: 2641812

(xi) SEQUENCE DESCRIPTION: SEQ ID NO:2:

ACTAGTTCTC TCTCTCTCTC TCCCGCGGGA GGCTACGCGC GGGGCGGGTG CTGCTTGCTG      60

CAGGCTCTGG GGAGTCGCCA TGCCTACAAC ACAGCAGTCC CCTCAGGATG AGCAGGAAAA     120

GCTCTTGGAT GAAGCCATAC AGGCTGTGAA GGTCCAGTCA TTCCAAATGA AGAGATGCCT     180

GGACAAAAAC AAGCTTATGG ATGCTCTAAA ACATGCTTCT AATATGCTTG GTGAACTCCG     240

GACTTCTATG TTATCACCAA AGAGTTACTA TGAACTTTAT ATGGCCATTT CTGATGAACT     300

GCACTACTTG GAGGTCTACC TGACAGATGA GTTTGCTAAA GGAAGGAAAG TGGCAGATCT     360

CTACGAACTT GTACAGTATG CTGGAAACAT TATCCCAAGG CTTTACCTTT TGATCACAGT     420

TGGAGTTGTA TATGTCAAGT CATTTCCTCA GTCCAGGAAG GATATTTTGA AGATTTGGT     480

AGAAATGTGC CGTGGTGTGC AACATCCCTT GAGGGGTCTG TTTCTTCGAA ATTACCTTCT     540

TCAGTGTACC AGAAATATCT TACCTGATGA AGGAGAGCCA ACAGATGAAG AAACAACTGG     600

TGACATCAGT GATTCCATGG ATTTTGTACT GCTCAACTTT GCAGAAATGA ACAAGCTCTG     660

GGTGCGAATG CAGCATCAGG ACATAGCCG AGATAGAGAA AAAAGAGAAC GAGAAAGACA     720

AGAACTGAGA ATTTTAGTGG GAACAAATTT GGTGCGCCTC AGTCAGTTGG AAGGTGTAAA     780

TGTGGAACGT ACAAACAGA TTGTTTTGAC TGGCATATTG GAGCAAGTTG TAAACTGTAG     840
```

-continued

```
GGATGCTTTG GCTCAAGAAT ATCTCATGGA GTGTATTATT CAGGTTTTCC CTGATGAATT      900

TCACCTCCAG ACTTTGAATC CTTTTCTTCG GGCCTGTGCT GAGTTACACC AGAATGTAAA      960

TGTGAAGAAC ATAATCATTG CTTTAATTGA TAGATTAGCT TTATTTGCTC ACCGTGAAGA     1020

TGGACCTGGA ATCCCAGCGG ATATTAAACT TTTTGATATA TTTTCACAGC AGGTGGCTAC     1080

AGTGATACAG TCTAGACAAG ACATGCCTTC AGAGGATGTT GTATCTTTAC AAGTCTCTCT     1140

GATTAATCTT GCCATGAAAT GTTACCCTGA TCGTGTGGAC TATGTTGATA AAGTTCTAGA     1200

AACAACAGTG GAGATATTCA ATAAGCTCAA CCTTGAACAT ATTGCTACCA GTAGTGCAGT     1260

TTCAAAGGAA CTCACCAGAC TTTTGAAAAT ACCAGTTGAC ACTTACAACA ATATTTTAAC     1320

AGTCTTGAAA TTAAAACATT TTCACCCACT CTTTGAGTAC TTTGACTACG AGTCCAGAAA     1380

GAGCATGAGT TGTTATGTGC TTAGTAATGT TCTGGATTAT AACACAGAAA TTGTCTCTCA     1440

AGACCAGGTG GATTCCATAA TGAATTTGGT ATCCACGTTG ATTCAAGATC AGCCAGATCA     1500

ACCTGTAGAA GACCCTGATC CAGAAGATTT TGCTGATGAG CAGAGCCTTG TGGGCCGCTT     1560

CATTCATCTG CTGCGCTCTG AGGACCCTGA CCAGCAGTAC TTGATTTTGA ACACAGCACG     1620

AAAACATTTT GGAGCTGGTG GAAATCAGCG GATTCGCTTC ACACTGCCAC CTTTGGTATT     1680

TGCAGCTTAC CAGCTGGCTT TTCGATATAA AGAGAATTCT AAAGTGGATG ACAAATGGGA     1740

AAAGAAATGC CAGAAGATTT TTTCATTTGC CCACCAGACT ATCAGTGCTT TGATCAAAGC     1800

AGAGCTGGCA GAATTGCCCT TAAGACTTTT TCTTCAAGGA GCACTAGCTG CTGGGGAAAT     1860

TGGTTTTGAA AATCATGAGA CAGTCGCATA TGAATTCATG TCCCAGGCAT TTTCTCTGTA     1920

TGAAGATGAA ATCAGCGATT CCAAAGCACA GCTAGCTGCC ATCACCTTGA TCATTGGCAC     1980

TTTTGAAAGG ATGAAGTGCT TCAGTGAAGA GAATCATGAA CCTCTGAGGA CTCAGTGTGC     2040

CCTTGCTGCA TCCAAACTTC TAAAGAAACC TGATCAGGGC CGAGCTGTGA GCACCTGTGC     2100

ACATCTCTTC TGGTCTGGCA GAAACACGGA CAAAAATGGG GAGGAGCTTC ACGGAGGCAA     2160

GAGGGTAATG GAGTGCCTAA AAAAAGCTCT AAAAATAGCA AATCAGTGCA TGGACCCCTC     2220

TCTACAAGTG CAGCTTTTTA TAGAAATTCT GAACAGATAT ATCTATTTTT ATGAAAAGGA     2280

AAATGATGCG GTAACAATTC AGGTTTTAAA CCAGCTTATC CAAAAGATTC GAGAAGACCT     2340

CCCGAATCTT GAATCCAGTG AAGAAACAGA GCAGATTAAC AAACATTTTC ATAACACACT     2400

GGAGCATTTG CGCTTGCGGC GGGAATCACC AGAATCCGAG GGGCCAATTT ATGAAGGTCT     2460

CATCCTTTAA AAAGGAAATA GCTCACCATA CTCCTTTCCA TGTACATCCA GTGAGGGTTT     2520

TATTACGCTA GGTTTCCCTT CCATAGATTG TGCCTTTCAG AAATGCTGAG GTAGGTTTCC     2580

CATTTCTTAC CTGTGATGTG TTTTACCCAG CACCTCCGGA CACTCACCTT CAGGACCTTA     2640

ATAAAATTAT TCACTTGGTA AGTGTTCAAG TCTTTCTGAT CACCCCAAGT AGCATGACTG     2700

ATCTGCAATT TAAAATTCCT GTGATCTGTA AAAAAAAAAA AAAAAAAAA AAAAAACAA      2760

AACCCACAAG CACTTATCTT GGCTACTAAT GAAGCTCTCC TTTTTTTTGT TGTTTGTTT     2820

GCTTCATTGT TGATTGTGTA TTTTCTTCAT TCCTGGGGAG TACTAACCCA AAAGCGTCTG    2880

TCTCTTGTTT TCTAGTCCAG TTTGAGATTA ATTTAGAAGA AAGGAATACT GTATGTGAAA    2940

TTCATCTTGG GCTTTCCCCT AAATTGCAAG ATAAGGCCAT GTGTAAGATT TTCCCTAAAA    3000

CTAGAATATA TTAATGCATG TTTGAGAATT TTAAAGCACC ATGGTCAAAA CCAGAAGCTA    3060

TATTTTGCAT ATTTGGACTC AGCCATCCAT TAAGAACCCA TGTTGTCCTC TGGACATATT    3120

TATCAATATA ATTGGGTTTT AAATAGTATA AAGAAAACT TGTGATCTAT ATAATTTATG     3180

TATCACCTTC ATTGTAAATT TAGCAGGAAA TGCATCACAA TTATGATTTT TTTTTTGCAC    3240
```

CAGTGA                                                                           3246

(2) INFORMATION FOR SEQ ID NO:3:

(i) SEQUENCE CHARACTERISTICS:
        (A) LENGTH: 754 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1354049

(xi) SEQUENCE DESCRIPTION: SEQ ID NO:3:

Met Pro Pro Ile Cys Leu Glu Ser Ser Gly Pro Leu Cys Cys His Gln
 1               5                  10                  15

Arg Val Thr Met Asn Phe Ile Trp Leu Phe Leu Met Asn Cys Thr Thr
             20                  25                  30

Trp Lys Val Tyr Leu Thr Asp Glu Phe Ala Lys Gly Glu Arg Leu Ala
         35                  40                  45

Asp Leu Tyr Glu Leu Val Gln Tyr Ser Gly Asn Ile Ile Pro Arg Leu
     50                  55                  60

Tyr Leu Leu Ile Thr Val Gly Val Val Tyr Lys Ser Phe Pro Gln
 65                  70                  75                  80

Ser Arg Lys Asp Ile Leu Lys Asp Leu Val Glu Met Cys Arg Gly Val
                 85                  90                  95

Gln His Pro Leu Arg Gly Leu Phe Leu Arg Asn Tyr Leu Leu Gln Cys
            100                 105                 110

Thr Arg Asn Ile Leu Pro Asp Glu Gly Glu Pro Thr Asp Glu Glu Thr
        115                 120                 125

Thr Gly Asp Ile Ser Asp Ser Met Asp Phe Val Leu Leu Asn Phe Ala
    130                 135                 140

Glu Met Asn Lys Leu Trp Val Arg Met Gln His Gln Gly His Ser Arg
145                 150                 155                 160

Asp Arg Glu Lys Arg Glu Arg Glu Arg Gln Glu Leu Arg Ile Leu Val
                165                 170                 175

Gly Thr Asn Leu Val Ala Leu Thr Leu Val Ser Trp Arg Cys Lys Cys
            180                 185                 190

Gly Thr Leu Gln Gln Ile Val Leu Thr Gly Ile Leu Glu Gln Val Val
        195                 200                 205

Asn Cys Arg Asp Ala Leu Ala Gln Glu Ile Ser Met Glu Cys Ile Ile
    210                 215                 220

Gln Val Phe Pro Asp Glu Phe His Leu Gln Thr Leu Asn Pro Phe Leu
225                 230                 235                 240

Arg Ala Cys Ala Glu Leu His Gln Asn Val Asn Val Lys Asn Ile Ile
                245                 250                 255

Ile Ala Leu Ile Asp Arg Leu Ala Leu Phe Ala His Arg Glu Met Glu
            260                 265                 270

Pro Gly Ile Pro Ala Glu Leu Lys Leu Phe Asp Ile Phe Ser Gln Gln
        275                 280                 285

Val Ala Thr Val Ile Gln Ser Arg Arg Asp Met Pro Ser Glu Asp Val
    290                 295                 300

Val Ser Leu Gln Val Ser Leu Ile Asn Leu Ala Met Lys Cys Tyr Pro
305                 310                 315                 320

Asp Arg Val Asp Tyr Val Asp Lys Val Leu Glu Thr Thr Val Glu Ile

-continued

```
                325                 330                 335
Phe Asn Lys Leu Asn Leu Glu His Ile Ala Thr Ser Ser Ala Val Ser
                340                 345                 350
Lys Glu Leu Thr Arg Leu Leu Lys Ile Pro Val Asp Thr Tyr Asn Asn
                355                 360                 365
Ile Leu Thr Val Leu Lys Leu Lys His Phe His Pro Leu Phe Glu Tyr
370                 375                 380
Phe Asp Tyr Glu Ser Ser Pro Gly Lys Ser Met Ser Cys Tyr Val Leu
385                 390                 395                 400
Ser Asn Val Leu Asp Tyr Asn Thr Glu Ile Val Ser Gln Asp Gln Val
                405                 410                 415
Asp Ser Ile Met Asn Leu Val Ser Thr Leu Ile Gln Asp Gln Pro Asp
                420                 425                 430
Gln Pro Val Glu Asp Pro Asp Pro Glu Asp Phe Ala Asp Glu Gln Ser
                435                 440                 445
Leu Val Gly Arg Phe Ile His Leu Leu Arg Ser Asp Asp Pro Asp Gln
450                 455                 460
Gln Tyr Leu Ile Leu Asn Thr Ala Arg Lys His Phe Gly Ala Gly Gly
465                 470                 475                 480
Asn Gln Arg Ile Arg Phe Thr Leu Pro Pro Leu Val Phe Ala Ala Tyr
                485                 490                 495
Gln Leu Ala Phe Arg Tyr Lys Glu Asn Ser Lys Trp Met Thr Ser Gly
                500                 505                 510
Lys Arg Asn Ala Arg Arg Tyr Phe His Leu Pro His Gln Thr Ile Ser
                515                 520                 525
Ala Leu Ile Lys Ala Glu Leu Ala Glu Leu Pro Leu Arg Leu Phe Leu
                530                 535                 540
Gln Gly Ala Leu Ala Ala Gly Glu Ile Gly Phe Glu Asn His Glu Thr
545                 550                 555                 560
Val Ala Tyr Glu Phe Met Ser Gln Ala Phe Ser Leu Tyr Glu Asp Glu
                565                 570                 575
Ile Ser Asp Ser Lys Ala Gln Leu Ala Ala Ile Thr Leu Ile Ile Gly
                580                 585                 590
Thr Phe Glu Arg Met Lys Cys Phe Ser Glu Glu Asn His Glu Pro Leu
                595                 600                 605
Arg Thr Glu Cys Ala Leu Ala Ala Ser Lys Leu Leu Lys Lys Pro Asp
                610                 615                 620
Gln Ala Glu Arg Glu His Met Cys Thr Ser Leu Trp Ser Gly Arg Asn
625                 630                 635                 640
Thr Asp Lys Asn Gly Glu Glu Leu His Gly Gly Lys Arg Val Met Glu
                645                 650                 655
Cys Leu Lys Lys Ala Leu Lys Ile Ala Asn Gln Cys Met Asp Pro Ser
                660                 665                 670
Leu Gln Val Gln Leu Phe Ile Glu Ile Leu Asn Arg Tyr Ile Tyr Phe
                675                 680                 685
Tyr Glu Lys Glu Asn Asp Ala Val Thr Ile Gln Val Leu Asn Gln Leu
                690                 695                 700
Ile Gln Lys Ile Arg Glu Asp Leu Pro Asn Leu Glu Ser Ser Glu Glu
705                 710                 715                 720
Thr Glu Gln Ile Asn Lys His Phe His Asn Thr Leu Glu His Leu Arg
                725                 730                 735
Thr Arg Arg Glu Ser Pro Glu Ser Glu Gly Pro Ile Tyr Glu Gly Leu
                740                 745                 750
```

Ile Leu (2) INFORMATION FOR SEQ ID NO:4:

(i) SEQUENCE CHARACTERISTICS:
        (A) LENGTH: 937 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 854543

(xi) SEQUENCE DESCRIPTION: SEQ ID NO:4:

```
Met Ala Tyr Ala Asp Ser Pro Glu Asn Ala Ile Ala Val Ile Lys Gln
  1               5                  10                  15

Arg Thr Ala Leu Met Asn Arg Cys Leu Ser Gln His Lys Leu Met Glu
             20                  25                  30

Ser Leu Gln His Thr Ser Ile Met Leu Thr Glu Leu Arg Asn Pro Asn
         35                  40                  45

Leu Ser Pro Lys Lys Tyr Tyr Glu Leu Tyr Val Ile Ile Phe Asp Ser
     50                  55                  60

Leu Thr Asn Leu Ser Thr Tyr Leu Ile Glu Asn His Pro Gln Asn His
 65                  70                  75                  80

His Leu Ala Asp Leu Tyr Glu Leu Val Gln Tyr Thr Gly Asn Val Val
                 85                  90                  95

Pro Arg Leu Tyr Leu Met Ile Thr Val Gly Thr Ser Tyr Leu Thr Phe
                100                 105                 110

Asn Glu Ala Pro Lys Lys Glu Ile Leu Lys Asp Met Ile Glu Met Cys
            115                 120                 125

Arg Gly Val Gln Asn Pro Ile Arg Gly Leu Phe Leu Arg Tyr Tyr Leu
        130                 135                 140

Ser Gln Arg Thr Lys Glu Leu Leu Pro Glu Asp Asp Pro Ser Phe Asn
145                 150                 155                 160

Ser Gln Phe Ile Met Asn Asn Phe Ile Glu Met Asn Lys Leu Trp Val
                165                 170                 175

Arg Leu Gln His Gln Gly Pro Leu Arg Glu Arg Glu Thr Arg Thr Arg
            180                 185                 190

Glu Arg Lys Glu Leu Gln Ile Leu Val Gly Ser Gln Leu Val Arg Leu
        195                 200                 205

Ser Gln Ile Ile Asp Asp Asn Phe Gln Met Tyr Lys Gln Asp Ile Leu
    210                 215                 220

Pro Thr Ile Leu Glu Gln Val Ile Gln Cys Arg Asp Leu Val Ser Gln
225                 230                 235                 240

Glu Tyr Leu Leu Asp Val Ile Cys Gln Val Phe Ala Asp Glu Phe His
                245                 250                 255

Leu Lys Thr Leu Asp Thr Leu Leu Gln Thr Thr Leu His Leu Asn Pro
            260                 265                 270

Asp Val Ser Ile Asn Lys Ile Val Leu Thr Leu Val Asp Arg Leu Asn
        275                 280                 285

Asp Tyr Val Thr Arg Gln Leu Glu Asp Asp Pro Asn Ala Thr Ser Thr
    290                 295                 300

Asn Ala Tyr Leu Asp Met Asp Val Phe Gly Thr Phe Trp Asp Tyr Leu
305                 310                 315                 320

Thr Val Leu Asn His Glu Arg Pro Asp Leu Ser Leu Gln Gln Phe Ile
```

-continued

```
                    325                 330                 335
Pro Leu Val Glu Ser Val Ile Val Leu Ser Leu Lys Trp Tyr Pro Asn
                340                 345                 350
Asn Phe Asp Asn Leu Asn Lys Leu Phe Glu Leu Val Leu Gln Lys Thr
                355                 360                 365
Lys Asp Tyr Gly Gln Lys Asn Ile Ser Leu Glu Ser Glu His Leu Phe
            370                 375                 380
Leu Val Leu Leu Ser Phe Gln Asn Ser Lys Leu Gln Leu Thr Ser Ser
385                 390                 395                 400
Thr Thr Ala Pro Pro Asn Ser Pro Val Thr Ser Lys Lys His Phe Ile
                405                 410                 415
Phe Gln Leu Ile Ser Gln Cys Gln Ala Tyr Lys Asn Ile Leu Ala Leu
                420                 425                 430
Gln Ser Ile Ser Leu Gln Lys Lys Val Val Asn Glu Ile Ile Asp Ile
            435                 440                 445
Leu Met Asp Arg Glu Val Glu Glu Met Ala Asp Asn Asp Ser Glu Ser
450                 455                 460
Lys Leu His Pro Gly His Ser Ala Tyr Leu Val Ile Glu Asp Lys
465                 470                 475                 480
Leu Gln Val Gln Arg Leu Leu Ser Ile Cys Glu Pro Leu Ile Ile Ser
                485                 490                 495
Arg Ser Gly Pro Pro Ala Asn Val Ala Ser Ser Asp Thr Asn Val Asp
            500                 505                 510
Glu Val Phe Phe Asn Arg His Asp Glu Glu Ser Trp Ile Leu Asp
            515                 520                 525
Pro Ile Gln Glu Lys Leu Ala His Leu Ile His Trp Ile Met Asn Thr
            530                 535                 540
Thr Ser Arg Lys Gln Thr Met Lys Asn Lys Ile Gln Phe Ser Leu Glu
545                 550                 555                 560
Ala Gln Leu Glu Ile Leu Leu Ile Lys Ser Ser Phe Ile Lys Gly
                565                 570                 575
Gly Ile Asn Val Lys Tyr Thr Phe Pro Ala Ile Ile Thr Asn Phe Trp
            580                 585                 590
Lys Leu Met Arg Lys Cys Arg Met Ile Gln Glu Tyr Leu Leu Lys Lys
                595                 600                 605
Arg Pro Asp Asn Lys Thr Leu Leu Ser His Tyr Ser Asn Leu Leu Lys
610                 615                 620
Gln Met Phe Lys Phe Val Ser Arg Cys Ile Asn Asp Ile Phe Asn Ser
625                 630                 635                 640
Cys Asn Asn Ser Cys Thr Asp Leu Ile Leu Lys Leu Asn Leu Gln Cys
                645                 650                 655
Ala Ile Leu Ala Asp Gln Leu Gln Leu Asn Glu Ile Ser Tyr Asp Phe
                660                 665                 670
Phe Ser Gln Ala Phe Thr Ile Phe Glu Glu Ser Leu Ser Asp Ser Lys
            675                 680                 685
Thr Gln Leu Gln Ala Leu Ile Tyr Ile Ala Gln Ser Leu Gln Lys Thr
            690                 695                 700
Arg Ser Leu Tyr Lys Glu Ala Tyr Tyr Asp Ser Leu Ile Val Arg Cys
705                 710                 715                 720
Thr Leu His Gly Ser Lys Leu Leu Lys Gln Asp Gln Cys Arg Ala
                725                 730                 735
Val Tyr Leu Cys Ser His Leu Trp Trp Ala Thr Glu Ile Ser Asn Ile
                740                 745                 750
```

-continued

```
Gly Glu Glu Glu Gly Ile Thr Asp Asn Phe Tyr Arg Asp Gly Lys Arg
        755                 760                 765

Val Leu Glu Cys Leu Gln Arg Ser Leu Arg Val Ala Asp Ser Ile Met
    770                 775                 780

Asp Asn Glu Gln Ser Cys Glu Leu Met Val Glu Ile Leu Asn Arg Cys
785                 790                 795                 800

Leu Tyr Tyr Phe Ile His Gly Asp Glu Ser Glu Thr His Ile Ser Ile
                805                 810                 815

Lys Tyr Ile Asn Gly Leu Ile Glu Leu Ile Lys Thr Asn Leu Lys Ser
            820                 825                 830

Leu Lys Leu Glu Asp Asn Ser Ala Ser Met Ile Thr Asn Ser Ile Ser
        835                 840                 845

Asp Leu His Ile Thr Gly Glu Asn Asn Val Lys Ala Ser Ser Asn Ala
850                 855                 860

Asp Asp Gly Ser Val Ile Thr Asp Lys Glu Ser Asn Val Ala Ile Gly
865                 870                 875                 880

Ser Asp Gly Thr Tyr Ile Gln Leu Asn Thr Leu Asn Gly Ser Ser Thr
                885                 890                 895

Leu Ile Arg Gly Val Val Ala Thr Ala Ser Gly Ser Lys Leu Leu His
            900                 905                 910

Gln Leu Lys Tyr Ile Pro Ile His His Phe Arg Arg Thr Cys Glu Tyr
        915                 920                 925

Ile Glu Ser Gln Arg Glu Val Asp Asp
        930                 935
```

What is claimed is:

1. An isolated and purified polynucleotide comprising SEQ ID NO:2.

2. An isolated and purified polynucleotide which is fully complementary to the polynucleotide of claim 1.

* * * * *